United States Patent
Yang et al.

(10) Patent No.: US 12,337,171 B2
(45) Date of Patent: Jun. 24, 2025

(54) IMPLANTABLE MEDICAL DEVICE

(71) Applicant: Medtronic, Inc., Minneapolis, MN (US)

(72) Inventors: Zhongping Yang, Woodbury, MN (US); Thomas A. Anderson, New Hope, MN (US); Kaileigh E. Rock, St. Paul, MN (US); Matthew D. Bonner, Plymouth, MN (US); Kathryn E. Hilpisch, Cottage Grove, MN (US); Wade M. Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 398 days.

(21) Appl. No.: 17/745,083

(22) Filed: May 16, 2022

(65) Prior Publication Data

US 2022/0395683 A1 Dec. 15, 2022

Related U.S. Application Data

(60) Provisional application No. 63/208,964, filed on Jun. 9, 2021.

(51) Int. Cl.
*A61N 1/00* (2006.01)
*A61N 1/05* (2006.01)
*A61N 1/375* (2006.01)

(52) U.S. Cl.
CPC ....... *A61N 1/0573* (2013.01); *A61N 1/37512* (2017.08); *A61N 1/37518* (2017.08); *A61N 1/3756* (2013.01)

(58) Field of Classification Search
None
See application file for complete search history.

(56) References Cited

U.S. PATENT DOCUMENTS 5,683,447 A * 11/1997 Bush ............... A61N 1/056
607/126
9,037,265 B2 5/2015 Ollivier
(Continued)

FOREIGN PATENT DOCUMENTS

WO 2020197854 A1 10/2020

OTHER PUBLICATIONS (PCT/US2022/030617) PCT Notification of Transmittal of the International Search Report and the Written Opinion of the International Searching Authority, dated Sep. 8, 2022, 10 pages.
(Continued)

*Primary Examiner* — Sana Sahand
(74) *Attorney, Agent, or Firm* — Shumaker & Sieffert, P.A.

(57) ABSTRACT

An implantable medical device configured to deliver pacing therapy, the implantable medical device including a device body configured to position within a heart, where the device body comprises a proximal body portion and a distal body portion and defines a longitudinal axis extending through the proximal body portion and the distal body portion, the proximal body portion is configured to rotate around the longitudinal axis relative to distal body portion, and a leadlet mechanically coupled to the device body, where the leadlet mechanically supports an electrode configured to deliver pacing therapy, and where in response to the proximal body portion rotating relative to the distal body portion, the device body is configured to alter an extension length of the leadlet.

19 Claims, 6 Drawing Sheets

(56) References Cited

U.S. PATENT DOCUMENTS

| | | | |
|---|---|---|---|
| 9,216,285 B1 | 12/2015 | Boling et al. | |
| 9,592,399 B2 | 3/2017 | Foster | |
| 10,894,167 B2 | 1/2021 | Koop et al. | |
| 2003/0204232 A1* | 10/2003 | Sommer | A61B 5/282 607/122 |
| 2006/0142814 A1* | 6/2006 | Laske | A61N 1/056 607/28 |
| 2009/0082828 A1* | 3/2009 | Ostroff | A61N 1/37205 607/9 |
| 2012/0172690 A1* | 7/2012 | Anderson | A61N 1/0573 607/18 |
| 2015/0165189 A1* | 6/2015 | Ollivier | A61N 1/37518 607/127 |
| 2019/0083779 A1 | 3/2019 | Yang et al. | |
| 2019/0083800 A1 | 3/2019 | Yang et al. | |
| 2019/0134413 A1 | 5/2019 | Mar et al. | |
| 2019/0160293 A1 | 5/2019 | Reinke et al. | |
| 2019/0240496 A1 | 8/2019 | Von Arx et al. | |
| 2020/0261715 A1 | 8/2020 | Eby et al. | |
| 2020/0306530 A1 | 10/2020 | Koop et al. | |
| 2021/0046306 A1 | 2/2021 | Grubac et al. | |

OTHER PUBLICATIONS

International Preliminary Report on Patentability from International Application No. PCT/US2022/030617 dated Nov. 21, 2023, 6 pp.

\* cited by examiner

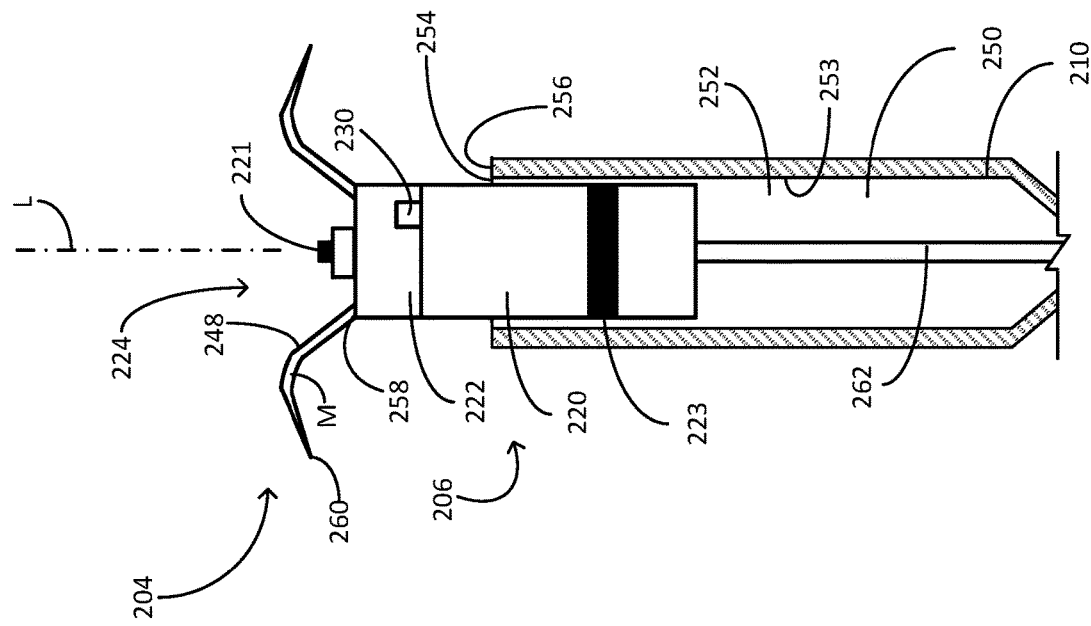
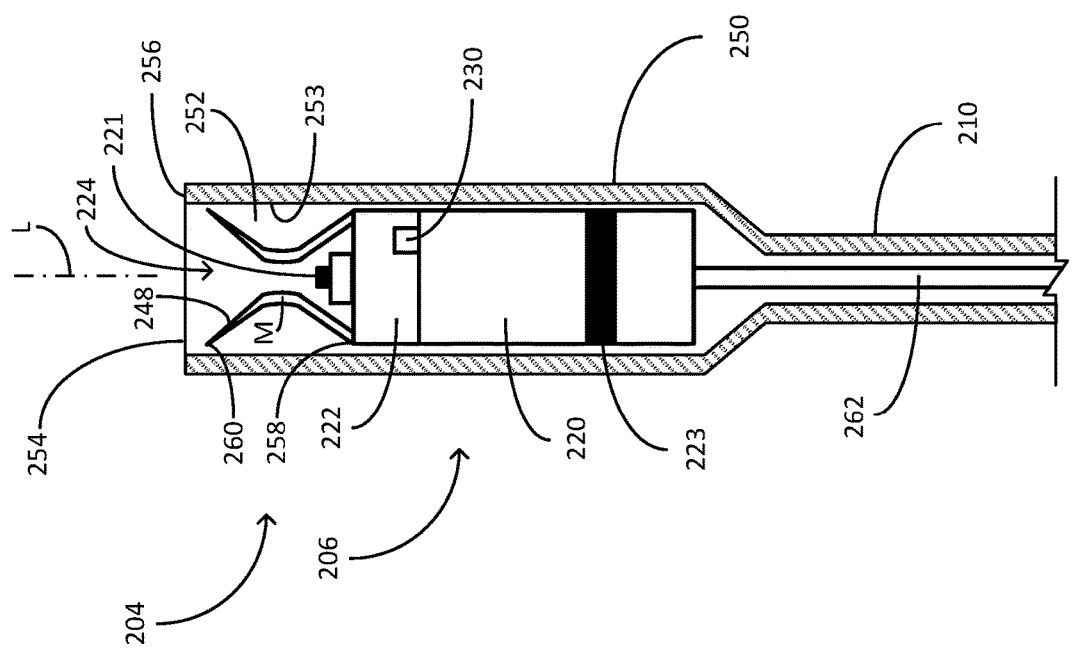
FIG. 4A
FIG. 4B

IMPLANTABLE MEDICAL DEVICE

TECHNICAL FIELD

This disclosure is related to an implantable medical systems, such as an implantable medical device.

BACKGROUND

Implantable medical devices are often placed in a subcutaneous pocket and coupled to one or more transvenous medical electrical leads carrying pacing and sensing electrodes positioned in the heart. Intracardiac pacemakers have recently been introduced that are implantable within a ventricular chamber of a patient's heart for delivering ventricular pacing pulses without the use of electrical leads. Such pacemakers or other implantable medical devices may also be able to detect the occurrence of arrhythmias, such as fibrillation, tachycardia and bradycardia, in the patient's heart. An implantable cardiac defibrillator may deliver electrical shocks to the patient's heart in response to detection of a tachycardia or fibrillation to restore a normal heartbeat in the patient. In some cases, a single implantable medical device functions as both an implantable pacemaker and implantable cardiac defibrillator.

Implantable medical devices may include electrodes and/or other elements for physiological sensing and/or therapy delivery. The electrodes and/or other elements may be implanted at target locations selected to detect a physiological condition of the patient and/or deliver one or more therapies. For example, the electrodes and/or other elements may be delivered to a target location within an atrium or ventricle to sense intrinsic cardiac signals and deliver pacing or antitachyarrhythmia shock therapy from a medical device coupled to a lead.

SUMMARY

This disclosure describes an implantable medical device (IMD) configured to position within a heart of a patient. The IMD includes a leadlet configured to extend over an extension length to cause a leadlet electrode to displace from a device body of the IMD. The device body includes a proximal body portion and a distal body portion. The distal body portion is configured to rotate relative to the proximal body portion to alter the extension length defined by the leadlet.

In an example, an implantable medical device configured to deliver pacing therapy, the implantable medical device including a device body configured to position within a heart, where the device body comprises a proximal body portion and a distal body portion and defines a longitudinal axis extending through the proximal body portion and the distal body portion, the proximal body portion is configured to rotate around the longitudinal axis relative to distal body portion, and a leadlet mechanically coupled to the device body, where the leadlet mechanically supports an electrode configured to deliver pacing therapy, and where in response to the proximal body portion rotating relative to the distal body portion, the device body is configured to alter an extension length of the leadlet.

In another example, an implantable medical device configured to deliver pacing therapy including a device body configured to position within a heart, wherein the device body comprises a proximal body portion and a distal body portion and defines a longitudinal axis extending through the proximal body portion and the distal body portion, and wherein the proximal body portion is configured to rotate around the longitudinal axis relative to distal body portion; a fixation mechanism attached to the distal body portion, wherein the fixation mechanism is configured to attach the implantable medical device to tissues of the heart; and a leadlet mechanically coupled to the device body, where the leadlet mechanically supports an electrode configured to deliver pacing therapy to a portion of a heart, in response to the proximal body portion rotating relative to the distal body portion, the device body is configured to alter an extension length of the leadlet, and the leadlet is configured to define a deployment configuration and a stowage configuration, where in the stowage configuration the leadlet is positioned within an outer boundary defined by the device body, and where the in the deployment configuration the leadlet is configured to extend over the extension length from the device body.

In another example, a method comprises: rotating a proximal body portion of a device body around a longitudinal axis of the implantable device and relative to a distal portion of the device body, wherein the device body is configured to position within a heart and comprises an implantable medical device; and altering an extension length of a leadlet attached to the device body and extending from the device body using the rotation of the proximal body portion relative to the distal body portion, wherein the leadlet mechanically supports an electrode.

The details of one or more examples are set forth in the accompanying drawings and the description below. Other features, objects, and advantages will be apparent from the description and drawings, and from the claims.

BRIEF DESCRIPTION OF DRAWINGS

FIG. 4A is a schematic illustration of an implantable medical device within a delivery catheter.

FIG. 4B is a schematic illustration of the implantable medical device of FIG. 4A with the delivery catheter withdrawn.

DETAILED DESCRIPTION

Figure 1:
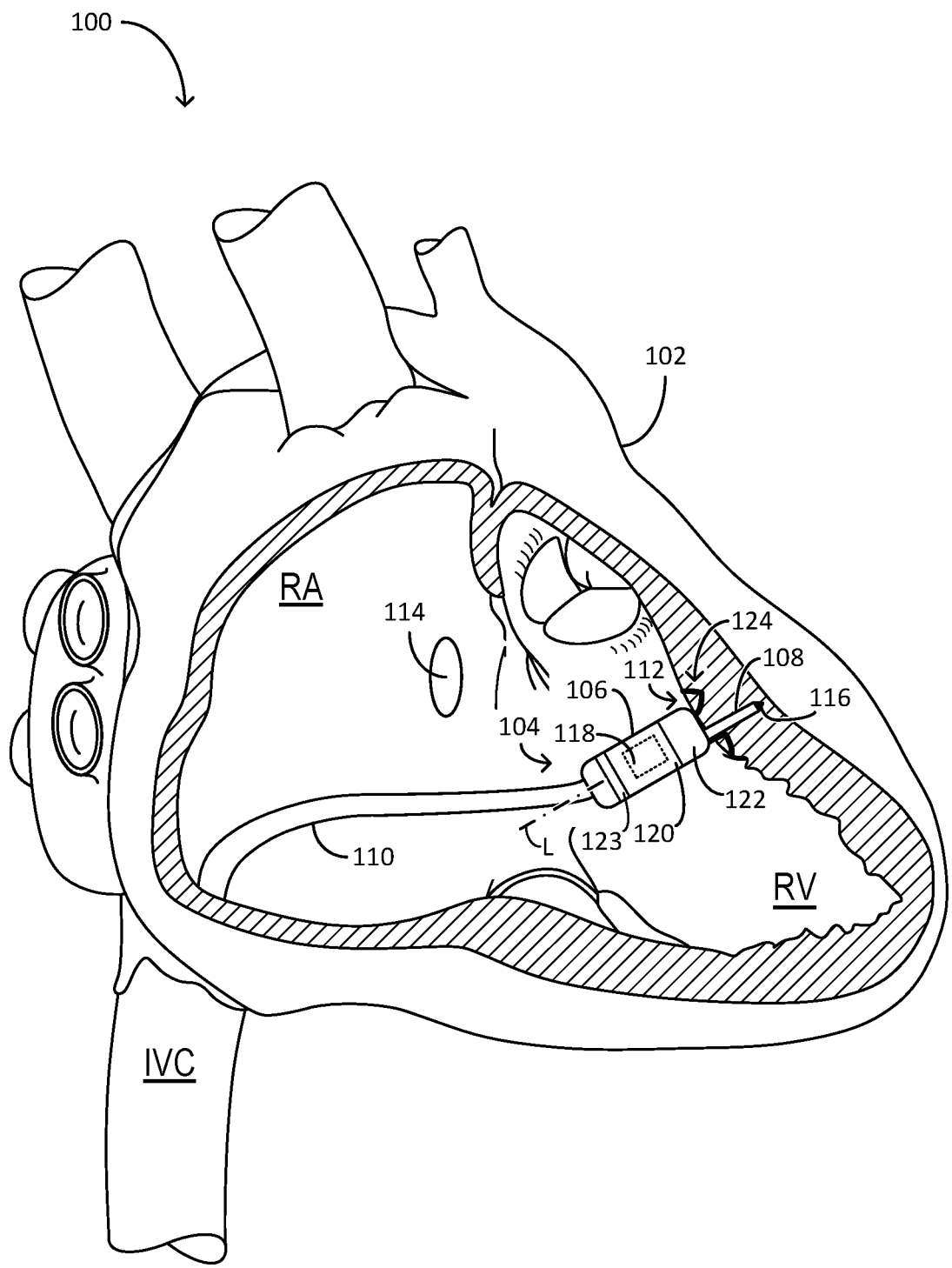
FIG. 1 is a conceptual diagram illustrating an example medical system including an implantable medical device.

This disclosure describes an implantable medical device (IMD) configured to implant a leadlet electrode within tissue of a patient, such as a septal wall of the heart. The IMD is configured to position within a heart of a patient, such as within an atrium, ventricle, coronary sinus, or other portions of the heart. The IMD includes a leadlet supporting the leadlet electrode and configured to deploy from a device body of the IMD. The IMD includes a proximal body portion configured to rotate relative to a distal body portion to cause deployment and/or adjust an extension length of the leadlet.

In some examples, the leadlet is configured to penetrate tissues of the heart. The leadlet may be configured to position the leadlet electrode within the tissues when the leadlet penetrates the tissues of the heart. In some examples, the leadlet electrode is a non-penetrating electrode, and the leadlet is configured to position the leadlet in contact with or in the vicinity of the tissues. The leadlet may be configured to position a physiological sensor configured to sense a physiological parameter of the patient (e.g., a blood pressure, a blood oxygen level, or another physiological parameter). The IMD may include a fixation mechanism configured to engage tissues of the heart to substantially affix the distal body portion to a target site within the heart. The IMD may be configured such that affixing the distal body portion to the target site substantially secures the distal body portion relative to the tissues, such that the proximal body portion may be rotated relative to the distal body portion (e.g., by a clinician) to cause the leadlet to extend from the device body to position the leadlet electrode.

The IMD is configured to alter an extension length of the leadlet when the proximal body portion rotates relative to the distal body portion such that, for example, a clinician may alter the extension length by causing rotation of the proximal body portion. In examples, the IMD is configured such that rotation of the proximal body portion relative to the distal body portion in a first rotational direction causes the leadlet to extend in a direction away from the device body. In examples, the IMD is configured such that rotation of the proximal body portion relative to the distal body portion in a second rotational direction (e.g., opposite the first rotational direction) causes the leadlet to retract in a direction toward the device body. The leadlet may be configured such that extension and/or retraction of the leadlet alters a displacement between the leadlet electrode and the device body. Hence, when the distal body portion is anchored to tissue (e.g., by the fixation mechanism) a clinician may cause a rotation of the proximal body portion to extend and/or retract the leadlet to position the leadlet electrode within tissues at a position from the device body.

The IMD may be configured for delivery and/or retrieval through vasculature of the patient for implantation within an atrium, ventricle, coronary sinus, or other portion of the heart. The IMD may be configured to be implanted and contained entirely within the body or boundary of the heart in contrast to traditional lead-based pacing devices which are implanted within the pectoral region of the patient with leads extending into the heart. The IMD may include a housing defining a volume configured to mechanically support circuitry. The circuitry may be configured to deliver therapy (e.g., pacing) to and/or sense signals from the heart using the leadlet electrode. In examples, the leadlet includes a conductor electrically connecting the leadlet electrode and circuitry. The leadlet may support any number of electrodes arranged in any configuration. In examples, the device body defines a return electrode electrically connected to the circuitry and the circuitry is configured to deliver therapy to and/or sense signals from the heart using the return electrode. In some examples, the distal body portion mechanically supports a second electrode (e.g., an atrial electrode), and the circuitry is configured to deliver therapy to and/or sense signals from the heart using the second electrode.

In examples, the device body defines an outer profile and the leadlet is configured to stow within the bounds of the outer profile until a rotation of the distal body portion causes the leadlet to extend from the device body. In some examples, the IMD is configured such that rotation of the proximal body portion relative to the distal body portion causes the extended leadlet to substantially retract back to within the outer profile defined by the device body from a deployment configuration. Hence, the IMD is configured such that the leadlet may be deployed from and/or returned to a stowage configuration wherein the leadlet is substantially within the outer profile of the device body. Establishing the leadlet in the stowage configuration may ease the delivery and/or retrieval of the IMD (e.g., by a clinician) through vasculature of the patient.

In examples, the device body defines a longitudinal axis and the proximal body portion is configured to rotate relative to the distal body portion around the longitudinal axis. The leadlet may be configured to at least partially coil around the longitudinal axis when the leadlet is in the stowage configuration. Rotation of the distal body portion relative to the proximal body portion (e.g., in a first rotational direction) may cause the leadlet to substantially spool out from the stowage condition to extend away from the device body. Rotation of the distal body portion relative to the proximal body portion (e.g., in a second rotational direction opposite the first rotational direction) may cause the extended leadlet to retract into the device body and substantially wind into the coiled configuration.

The leadlet may define an extension length between a distal end of the leadlet ("leadlet distal end") and the device body. In examples, the device body defines a leadlet access configured to allow the leadlet to pass therethrough, and the extension length is a length of the leadlet between the leadlet access and the leadlet distal end. In some examples, the extension length is a displacement between the leadlet distal end and a fixed point on the device body. The IMD may be configured such that rotation of the proximal body portion relative to the distal body portion alters the extension length. In examples, the IMD is configured to impart a first force in a first direction to the leadlet to increase the extension length. In examples, the IMD is configured to impart a second force in a second direction opposite the first direction to decrease the extension length. In some examples, a proximal end of the leadlet ("leadlet proximal end") is secured to the device body, and the device body is configured to impart the first force and/or the second force on the leadlet proximal end when the proximal body portion rotates relative to the distal body portion.

The IMD may be configured to cause the leadlet to extend from the device body in any direction relative to the longitudinal axis defined by the device body. In some examples, the IMD is configured to cause the leadlet to extend in a particular direction relative to the longitudinal axis. For example, the IMD may be configured to cause the leadlet to extend in a direction substantially perpendicular to the longitudinal axis when the leadlet extends from the device body. The IMD may be configured to cause the leadlet to extend in a direction substantially parallel to the longitudinal axis when the leadlet extends from the device body. In some examples, the IMD (e.g., some portion of the distal body portion) is configured to insert into a coronary sinus of the heart and cause the leadlet to extend substantially perpendicular to the longitudinal axis to implant the leadlet electrode within a ventricular wall when the IMD is inserted in the coronary sinus. In some examples, the IMD is configured to affix to a septum of the heart (e.g., an atrial and/or ventricular septum) and cause the leadlet to extend substantially parallel to the longitudinal axis to implant the leadlet electrode within the septum. The leadlet may include a shape-memory material (e.g., a shape-memory polymer, a shape memory alloy such as Nitinol, or some other shape memory material) which tends to cause the leadlet to extend in the particular direction relative to the longitudinal axis. In some examples, a location of the leadlet access on the device body may tend to cause the leadlet to extend in the particular direction.

The IMD is configured to transit through vasculature of the patient to position the IMD in the vicinity of a target area, such as an area within a chamber of the heart. For example, the IMD may be configured to allow a clinician to navigate the IMD through a vein of the heart (e.g., an innominate vein, an interior vena cava (IVC), a superior vena cava (SVC), or another venous pathway) to a target location within a right ventricle (RV), right atrium (RA), or another area of the heart. In examples, the IMD is configured to position with a lumen of a delivery catheter configured to transit the IMD through vasculature. For example, the delivery catheter may include a cup section at a distal end of the catheter configured to substantially hold the IMD as the delivery catheter transits through vasculature. The IMD may be configured to fit within a lumen defined by the cup section when the leadlet is in the stowage configuration (e.g., when the leadlet is stowed within the bounds of the outer profile defined by the device body).

FIG. 1 is a conceptual diagram illustrating a portion of an example medical system 100 configured to deliver therapy (e.g., pacing) to a heart 102 of a patient. Medical system 100 includes IMD 104 including device body 106 and leadlet 108 extending from device body 106. Medical system 100 includes a delivery catheter 110 configured to position IMD 104 within the vicinity of a target site 112 within heart 102. In examples, as illustrated in FIG. 1, target site 112 is a region in a ventricular wall of the right ventricle (RV) of heart 102. In other examples, delivery catheter 110 and/or IMD 104 may be configured to position in the vicinity of a target site at another portion of heart 102. For example, delivery catheter 110 and/or IMD 104 implantable medical lead may be configured to position in the vicinity of a target site in the right atrium (RA) of heart 102, the left atrium (not shown), the left ventricle (not shown), or within or around the coronary sinus 114. Delivery catheter 110 and IMD 104 may be configured to extend through vasculature of a patient (e.g., an interior vena cava (IVC)) to position IMD 104 within heart 102. In examples, delivery catheter 110 includes a cup section (not shown) defining a lumen configured to engage IMD 104.

IMD 104 may include a fixation mechanism 124 configured to secure IMD 104 to tissues of heart 102 such that IMD 104 is contained within the body or perimeter of the heart. In examples, device body 106 mechanically supports fixation mechanism 124. Fixation mechanism 124 is configured to penetrate tissue of heart 102 at or near a target site, such as target site 112. For example, fixation mechanism 124 may be configured to penetrate cardiac tissue of a septal wall in a RV, RA, LV, and/or LA of heart 102, or penetrate cardiac tissue in another area of heart 102. Fixation mechanism 124 may be configured to substantially maintain IMD 104 at or in the vicinity of the target site when fixation mechanism 124 penetrates tissues at or in the vicinity of the target site.

Fixation mechanism 124 may be configured to allow a clinician to cause fixation mechanism 124 to engage the tissue within heart 102, such that the clinician may affix IMD 104 once delivered to the target site. For example, fixation mechanism 124 may include one or more tines configured to position within the cup section of delivery catheter 110 when IMD 104 is positioned within the cup section, with the one or more tines resiliently biased to deploy outward to grasp tissue when delivery catheter 110 is proximally withdrawn (e.g., by the clinician). In some examples, fixation mechanism 124 may include a helical element, a barbed element, screws, rings, and/or other structures configured to resist a translation (e.g., a proximal translation) of device body 106 away from a tissue wall when fixation mechanism 124 is engaged with the tissue wall. Hence, medical system 100 may be configured such that a clinician may guide IMD 104 to the vicinity of a target site such as target site 112 using delivery catheter 110, then cause fixation mechanism 124 to substantially maintain IMD 104 at or in the vicinity of the target site.

IMD 104 may be configured such that, when attached to tissues of heart 102 by fixation mechanism 124, leadlet 108 may be deployed from device body 106 to penetrate tissues of heart 102. Leadlet 108 may be configured to deploy from device body 106 to penetrate tissues in the vicinity of a target site such as target site 112. Leadlet 108 mechanically supports a leadlet electrode 116. In examples, leadlet 108 may be configured to deploy from device body 106 to position leadlet electrode 116 within tissues of heart 102 and substantially displaced from device body 106. IMD 104 is configured to alter a length of leadlet 108 which extends from device body 106 such that, for example, leadlet 108 may establish and/or alter the position of leadlet electrode 116 within the tissue of heart 102. In examples, device body 106 is configured to mechanically support circuitry 118 configured to deliver therapy (e.g., pacing) to and/or sense signals from heart 102 using leadlet electrode 116. Leadlet 108 may include a conductor (not shown) electrically connecting leadlet electrode 116 and circuitry 118.

Device body 106 includes a proximal body portion 120 and a distal body portion 122. Proximal body portion 120 is configured to rotate relative to distal body portion 122 around a longitudinal axis L defined by device body 106. IMD 104 is configured to alter an extension length of leadlet 108 when proximal body portion 120 rotates relative to distal body portion 122. For example, IMD 104 may be configured to cause an extension of leadlet 108 in a direction substantially away from device body 106 when proximal body portion 120 rotates relative to distal body portion 122. In examples, IMD 104 is configured to cause a retraction of leadlet 108 in a direction substantially toward device body 106 when proximal body portion 120 rotates relative to distal body portion 122. Distal body portion 122 may mechanically support fixation mechanism 124 and be configured to remain rotationally stationary with respect to fixation mechanism 124. Hence, IMD 104 may be configured such that, when fixation mechanism 124 engages tissues of heart 102 and a torque around longitudinal axis L is exerted on proximal body portion 120 (e.g., by delivery catheter 110 or another device), the torque causes proximal body portion 120 to rotate relative to distal body portion 122 such that leadlet 108 extends or retracts.

Leadlet 108 may be configured such that extension and/or retraction of leadlet 108 alters a displacement between leadlet electrode 116 and device body 106. Hence, when distal body portion 122 is anchored to tissue by fixation mechanism 124, a clinician may cause a torque around longitudinal axis L to be exerted on proximal body portion 120 extend and/or retract leadlet 108 to position leadlet electrode 116 within tissues of heart 102. In examples, leadlet electrode 116 is configured to substantially implant within tissues of heart 102 to conduct electrical signals from circuitry 118 to the target tissue of heart 102, such that the electrical signals cause the cardiac muscle, e.g., of the ventricles, to depolarize and, in turn, contract at a regular interval.

IMD 104 may be configured to cause leadlet 108 to extend from device body 106 in any direction relative to longitudinal axis L when proximal body portion 120 rotates relative to distal body portion 122. In examples, as illustrated in FIG. 1, IMD 104 is configured to cause leadlet 108 to extend from device body 106 in a direction substantially parallel to longitudinal axis L when proximal body portion 120 rotates relative to distal body portion 122. In other examples, IMD 104 is configured to cause leadlet 108 to extend from device body 106 in a direction substantially perpendicular to longitudinal axis L when proximal body portion 120 rotates relative to distal body portion 122. In some examples, IMD 104 is configured such that some portion of device body 106 (e.g., fixation mechanism 124 and distal body portion 122) inserts within coronary sinus 114 and leadlet 108 deploys substantially perpendicular to longitudinal axis L to penetrate tissues defining a wall of coronary sinus 114.

Hence, medical system 100 may be configured to position IMD 104 at or in the vicinity of a target site using delivery catheter 110. Fixation mechanism 124 may be caused (e.g., by a clinician) to substantially affix distal body portion 122 to the target site, such that distal body portion 122 remains substantially stationary with respect to tissues at the target site. Leadlet 108 may be deployed from device body 106 to position leadlet electrode 116 within tissues of heart 102. In examples, leadlet 108 is deployed by causing (e.g., by a clinician) a rotation of proximal body portion 120 relative to distal body portion 122. In examples, leadlet 108 may be deployed by exerting a force on leadlet 108 using, for example, a stylet. IMD 104 is configured such that rotation of proximal body portion 120 relative to distal body portion 122 causes leadlet 108 to extend and/or retract relative to device body 106.

Figure 2B:
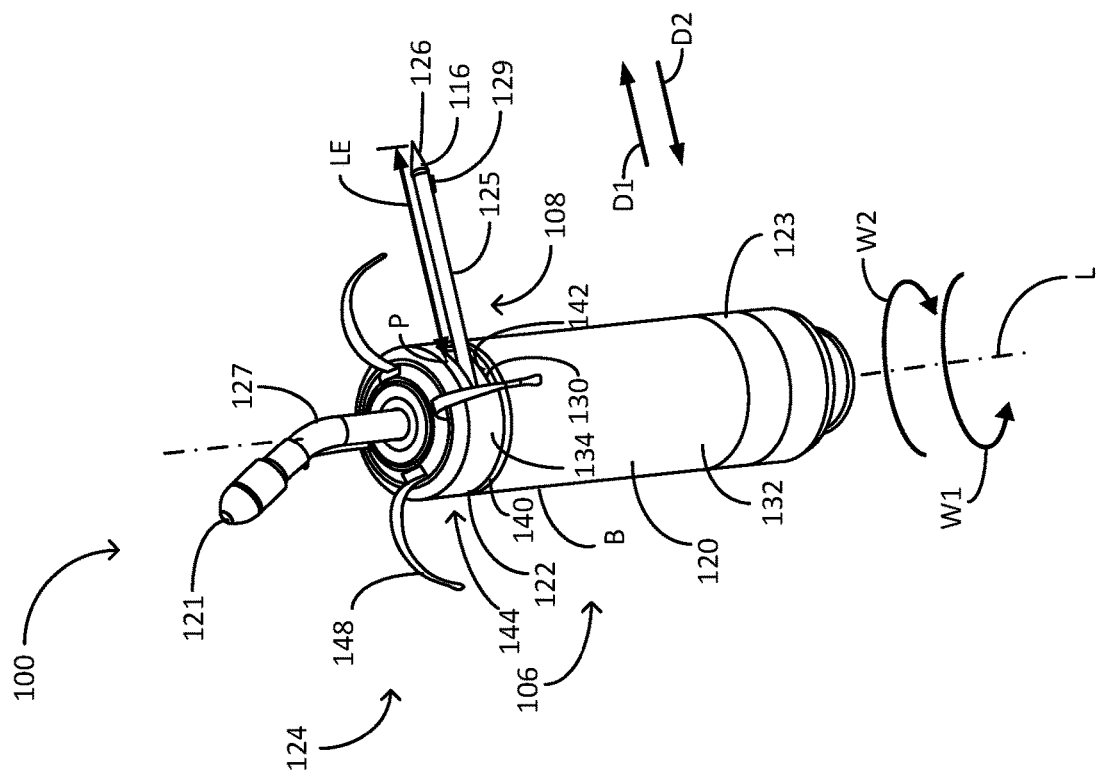
FIG. 2B is a perspective view of the implantable medical device of FIG. 2A with the leadlet extending substantially perpendicular to a longitudinal axis.
Figure 2A:
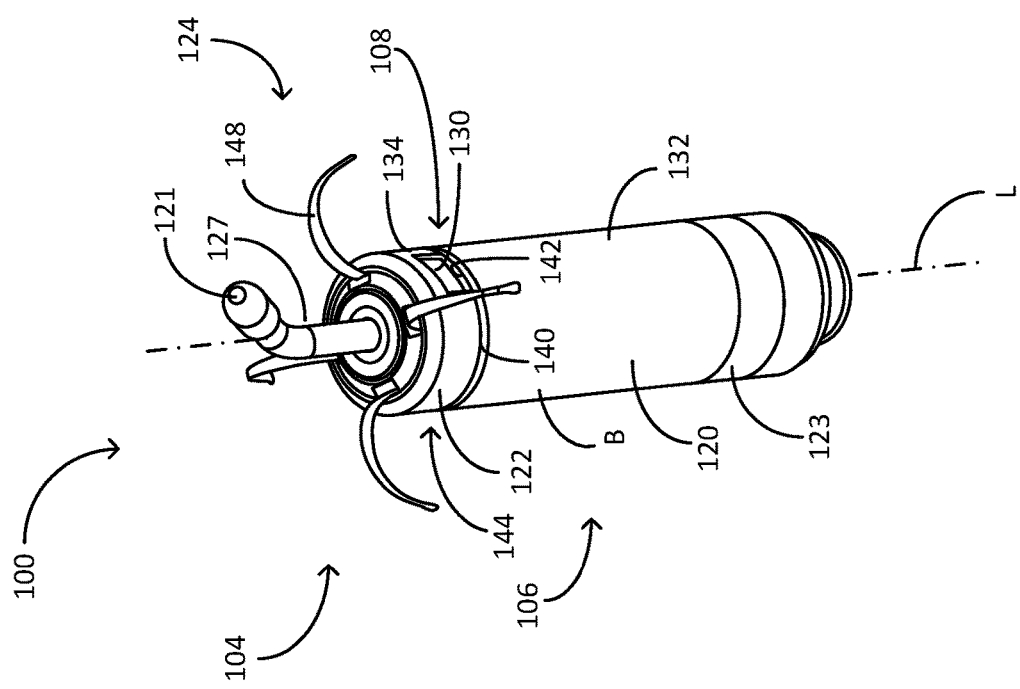
FIG. 2A is a perspective view of an implantable medical device with a leadlet in a stowage configuration.
Figure 3:
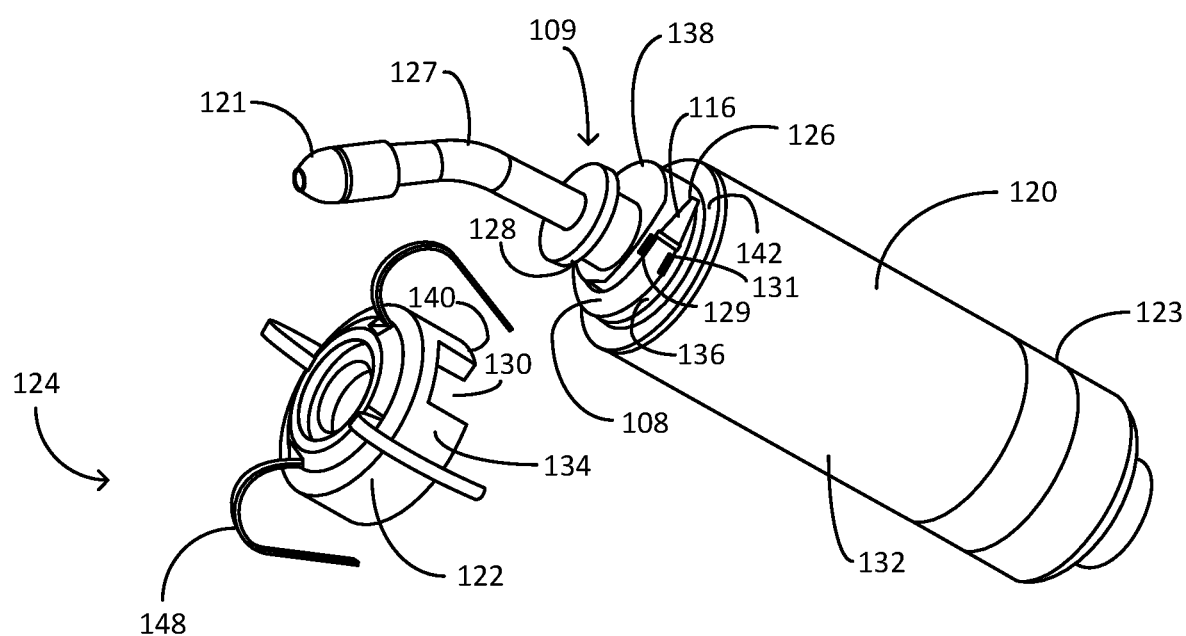
FIG. 3 is an exploded view showing a distal body portion and a proximal body portion of the implantable medical device of FIG. 2A and FIG. 2B.

FIG. 2A and FIG. 2B illustrate medical system 100 including a perspective view of an example IMD 104. FIG. 2A illustrates IMD 104 with leadlet 108 is a stowed configuration, such that leadlet 108 is positioned within an outer boundary B defined by device body 106. FIG. 2B illustrates IMD 104 leadlet 108 in a deployed configuration, with proximal body portion 120 having rotated around longitudinal axis L to cause leadlet 108 to extend over an extension length LE away from device body 106. FIG. 3 illustrates an exploded view of IMD 104, illustrating distal body portion 122 separated from proximal body portion 120 and leadlet 108 positioned to stow within a stowage volume defined by proximal body portion 120 and distal body portion 122.

As illustrated in FIGS. 2A and 2B, device body 106 defines a longitudinal axis L extending through proximal body portion 120 and distal body portion 122. Proximal body portion 120 is configured to rotate around longitudinal axis L relative to distal body portion 122. In examples, proximal body portion 120 is configured to rotate around longitudinal axis L relative to distal body portion 122 in a first rotational direction W1 and/or a second rotational direction W2 opposite the first rotational direction W1. It is understood that, when proximal body portion 120 rotates relative to distal body portion 122 as described herein, this may result from a rotation of proximal body portion 120 around longitudinal axis L as distal body portion 122 remains substantially stationary, or a rotation of distal body portion 122 around longitudinal axis L as proximal body portion 120 remains substantially stationary, or a rotation of both proximal body portion 120 and distal body portion 122 around longitudinal axis L at differing directions and/or speeds of rotation.

IMD 104 is configured such that proximal body portion 120 may rotate relative to distal body portion 122 to alter the extension length LE of leadlet 108. IMD 104 may be configured such that a rotation of proximal body portion 120 relative to distal body portion causes an increase and/or decrease in the extension length LE. In examples, IMD 104 is configured such that when distal body portion 122 is anchored to tissue by fixation mechanism 124, a clinician may cause a torque around longitudinal axis L to be exerted on proximal body portion 120 extend and/or retract leadlet 108. In examples, IMD 104 includes and/or defines a rotary joint 109 (FIG. 3) configured to operably connect to proximal body portion 120 and distal body portion 122 to allow proximal body portion 120 to rotate relative to distal body portion 122. Rotary joint 109 may be configured to limit a linear displacement parallel to longitudinal axis L between proximal body portion 120 and distal body portion 122 while allowing the rotation. In examples, rotary joint 109 is configured such that when one of distal body portion 122 or proximal body portion 120 exerts a force parallel to longitudinal axis L on the other of distal body portion 122 or proximal body portion 120, distal body portion 122 and proximal body portion 120 generate an action-reaction force pair substantially limiting and/or eliminating the linear displacement.

Leadlet 108 includes a leadlet body 125 defining a distal end 126 of leadlet body 125 ("leadlet distal end 126"). Leadlet body 125 may be an elongated body defining a proximal end 128 of leadlet body 125 ("leadlet proximal end 128" (FIG. 3)) opposite leadlet distal end 126. In examples, leadlet proximal end 128 is secured to device body 106 and leadlet distal end 126 is a substantially free end. In some examples, leadlet proximal end 128 is secured to proximal body portion 120. Leadlet proximal end 128 may be configured to rotate around longitudinal axis L when proximal body portion 120 rotates around longitudinal axis L.

Leadlet 108 mechanically supports one or more electrodes such as leadlet electrode 116. Leadlet 108 may support any number of electrodes arranged in any configuration. In examples, leadlet 108 mechanically supports leadlet electrode 116 substantially at leadlet distal end 126. In some examples, leadlet 108 mechanically supports leadlet electrode 116 such that leadlet electrode 116 substantially defines leadlet distal end 126. In examples, leadlet 108 includes a conductor (not shown) electrically connected to leadlet electrode 116. The conductor may be configured to electrically connect leadlet electrode 116 with circuitry 118 (FIG. 1) configured to deliver therapy (e.g., pacing) to and/or sense signals from heart 102 using leadlet electrode 116.

In examples, device body 106 defines a return electrode 123 electrically connected to circuitry 118. Circuitry 118 may be configured to deliver therapy to and/or sense signals from heart 102 using return electrode 123. In some examples, device body 106 (e.g., proximal body portion 120 or distal body portion 122) mechanically supports a second electrode 121 (e.g., an atrial electrode), and circuitry 118 is configured to deliver therapy to and/or sense signals from heart 102 using second electrode 121. Second electrode 121 may be configured to contact and/or penetrate tissues of heart 102 when fixation mechanism 124 engages tissues of heart 102. In some examples, IMD 104 includes a stem member 127 extending from device body 106 defining a displacement between second electrode 121 and distal body portion 122. In some examples, second electrode 121 may be a button electrode configured to contact tissues of heart 102 when device body 106 (e.g., distal body portion 122) contacts tissues of heart 102. Circuitry 118 may be configured to deliver therapy (e.g., pacing) to and/or sense signals from heart 102 using any of leadlet electrode 116, second electrode 121, and/or return electrode 123.

Leadlet 108 is configured to extend from device body 106 to define the extension length LE. In examples, extension length LE is a displacement between leadlet distal end 126 and device body 106. In some examples, device body 106 defines a leadlet access 130 configured to allow leadlet 108 to pass therethrough, and extension length LE is a length of leadlet 108 between leadlet access 130 and leadlet distal end 126. In some examples, extension length LE is a displacement between leadlet distal end 126 and a fixed point P on device body 106 (e.g., on distal body portion 122). IMD 104 is configured to alter (e.g., increase and/or decrease) the extension length LE of leadlet 108 when proximal body portion 120 rotates relative to distal body portion 122. Hence, IMD 104 is configured such that clinician may cause a rotation of proximal body portion 120 (e.g., using delivery catheter 110 (FIG. 1)) relative to distal body portion 122 to cause an alteration of the extension length LE such that, for example, leadlet 108 alters a position of leadlet electrode 116.

In examples, IMD 104 is configured to exert a force on leadlet 108 to cause leadlet 108 to alter the extension length LE when proximal body portion 120 rotates relative to distal body portion 122. For example, leadlet proximal end 128 may be secured to proximal body portion 120 such that leadlet proximal end 128 rotates around longitudinal axis L when proximal body portion 120 rotates around longitudinal axis L. Proximal body portion 120 may exert a torque on leadlet proximal end 128 (e.g., in the first rotational direction W1 and/or the second rotational direction W2) causing leadlet proximal end 128 to receive the force from proximal body portion 120 and transmit the force along leadlet body 125. The force received by leadlet proximal end 128 and transmitted along leadlet body may cause leadlet body 125 to translate (e.g., through leadlet access 130) to increase and/or decrease the extension length LE. In examples, IMD 104 is configured to impart a force in a first direction D1 on leadlet 108 to increase the extension length LE when proximal body portion 120 rotates in the first rotational direction W1 relative to distal body portion 122. In examples, IMD 104 is configured to impart a force in a second direction D2 on leadlet 108 to decrease the extension length LE when proximal body portion 120 rotates in the second rotational direction W2 relative to distal body portion 122.

In examples, instead of or in addition to transferring a torque to leadlet proximal end 128, proximal body portion 120 may be configured to mechanically engage leadlet body 125 to transfer a force to leadlet 108 as proximal body portion 120 rotates relative to distal body portion 122, such that the force causes leadlet 108 to translate to alter the extension length LE. Proximal body portion 120 may include an engaging structure 131 (FIG. 3) configured to rotate when proximal body portion 120 rotates. Engaging structure 131 may be configured to contact leadlet body 125 and generate a frictional force on leadlet body 125 when engaging structure 131 rotates with proximal body portion 120. Engaging structure 131 and/or leadlet body 125 may be configured such the frictional force imparts a force on leadlet body 125, causing movement of leadlet 108.

IMD 104 may be configured such that the extension length LE of leadlet 108 may be increased without a relative rotation between proximal body portion 120 and distal body portion 122. For example, leadlet 108 (e.g., leadlet body 125, leadlet distal end 126, leadlet electrode 116, and/or another portion of leadlet 108) may include a bearing structure 129 (FIG. 2B) configured to receive an elongated body such as a stylet. Bearing structure 129 may be configured to receive a force (e.g., in the direction D1 and/or D2) and transfer the force to leadlet 108 to cause a translation of leadlet 108 relative to device body 106. In examples, IMD 104 is configured such that leadlet 108 may translate in at least one direction (e.g., in the direction D1 or D2) when proximal body portion 120 is substantially rotationally stationary with respect to distal body portion 122. For example, IMD 104 may be configured to allow leadlet 108 to translate in the first direction D1 when proximal body portion 120 is substantially rotationally stationary with respect to distal body portion 122, such that, for example, a clinician may extend leadlet 108 by using the elongated body to exert a force on bearing structure 129 as proximal body portion 120 remains rotationally stationary with respect to distal body portion 122. In other examples, IMD 104 may be configured such that a force exerted on bearing structure 129 to increase or decrease the extension length LE causes and/or results in rotation of proximal body portion 120 relative to distal body portion 122. Hence, IMD 104 may be configured such that a clinician may exert a force on bearing structure 129 to cause leadlet 108 to position leadlet electrode 116 at a desired location within the tissue of heart 102.

In some examples, leadlet body 125 is configured to receive a force from proximal body portion 120 and transfer the force to leadlet distal end 126 to cause leadlet distal end 126 to penetrate tissues of heart 102. Leadlet body 125 may be configured to remain substantially stiff as leadlet body 125 transfers the force to leadlet distal end 126, such that the penetration of tissue by leadlet distal end 126 may substantially be caused by a rotation of proximal body portion 120 relative to distal body portion 122. For example, IMD 104 may be configured such that, when fixation mechanism 124 secures distal body portion 122 to tissue in a target site and proximal body portion 120 rotates around longitudinal axis L, the rotation of proximal body portion 120 imparts a force to leadlet body 125 increasing the extension length LE of leadlet 108 and causing leadlet distal end 126 to contact tissues in the target site. Leadlet body 125 may have a stiffness such that leadlet body 125 transfers force to leadlet distal end 126 sufficient to cause leadlet distal end 126 to penetrate the tissues in the target site as rotation of proximal body portion 120 continues. Hence, IMD 104 may be configured such that a clinician may position leadlet electrode 116 at a desired location within heart 102 using a rotation of proximal body portion 120 relative to distal body portion 122. In examples, leadlet distal end 126 defines a shape configured to facilitate penetration into the tissue such as, for example, a substantially sharp shape, a shape defining an substantially pointed apex, or some other shape configured to facilitate penetration when leadlet body 125 transfers a force to leadlet distal end 126.

As discussed, although depicted in FIG. 2B as extending substantially perpendicular to longitudinal axis L. IMD 104 may be configured to cause leadlet 108 to extend in any direction relative to longitudinal axis L in other examples. In some examples, IMD 104 includes a directing structure 136 (FIG. 3) configured to cause leadlet 108 to extend in a particular direction relative to longitudinal axis L when proximal body portion 120 rotates relative to distal body portion 122 to impart a force on leadlet proximal end 128.

In examples, as illustrated in FIG. 3, proximal body portion 120 defines at least some portion of directing structure 136. In other examples, distal body portion 122 defines at least some portion of directing structure 136. Directing structure 136 may be a platform and/or ramp configured to direct leadlet 108 (e.g., leadlet body 125) in a specific direction relative to longitudinal axis L when device body 106 imparts a force on leadlet proximal end 128. Directing structure 136 may be configured to substantially direct leadlet distal end 126 through leadlet access 130 to cause leadlet 108 to extend in a direction away from device body 106 when proximal body portion 120 rotates relative to distal body portion 122.

In some examples, leadlet body 125 includes a shape-memory material biased to extend in a certain direction relative to longitudinal axis L when leadlet 108 extends away from device body 106. Leadlet body 125 may be configured such that, when a section of leadlet body is in a substantially relaxed condition (e.g., free of external forces imparted by device body 106), the resilient biasing of the shape memory material tends to cause leadlet body 125 to extend in the specific direction. The shape memory material may be resiliently biased such that leadlet body 125 tends to extend in a specific direction substantially perpendicular to longitudinal axis L, in a specific direction substantially parallel to longitudinal axis L, or in any other specific direction relative to longitudinal axis L.

Leadlet access 130 may be defined anywhere on device body 106, and may be configured to allow an extension of leadlet 108 in any direction relative to longitudinal axis L. In examples leadlet access 130 is defined by distal body portion 122. Leadlet access 130 may be configured to allow passage of leadlet distal end 126 and/or leadlet body 125 therethrough when directing structure 136 directs leadlet distal end 126 and/or leadlet body 125 in a specific direction relative to longitudinal axis L. In examples, leadlet access 130 is configured such that leadlet 108 translates over a path between directing structure 136 and leadlet access 130 when leadlet proximal end 128 receives force from device body 106 (e.g., proximal body portion 120).

In examples, device body 106 defines an axial portion 138 (FIG. 3) extending from proximal body portion 120 and configured to allow proximal body portion 120 to rotate relative to distal body portion 122. Axial portion 138 may be configured to rotate when proximal body portion 120 rotates. In examples, axial portion 138 is configured to rotate within an inner perimeter defined by the distal body portion 122. IMD 104 may be configured such that longitudinal axis L intersects axial portion 138. Axial portion 138 may be configured to rotate around longitudinal axis L when proximal body portion 120 rotates around longitudinal axis L. In examples, axial portion 138 defines at least some portion of rotary joint 109. Distal body portion 122 may be configured to at least partially surround axial portion 138 when rotary joint 109 operably couples distal body portion 122 and proximal body portion 120. In examples, distal body portion 122 is configured to substantially cover axial portion 138 when rotary joint 109 operably couples distal body portion 122 and proximal body portion 120. In some examples, distal body portion 122 defines a base surface 140 ("distal portion base surface 140) and proximal body portion 120 defines a base surface 142 ("proximal portion base surface 142), and distal portion base surface 140 is configured to substantially face proximal portion base surface 142 when distal body portion 122 at least partially surround axial portion 138. Distal portion base surface 140 may be configured to substantially face proximal portion base surface 142 when rotary joint 109 operable couples distal body portion 122 and proximal body portion 120. In some examples, distal portion base surface 140 and distal portion base surface 142 are configured to define substantially parallel surfaces when distal body portion 122 at least partially surround axial portion 138 and/or rotary joint 109 operable couples distal body portion 122 and proximal body portion 120.

In examples, IMD 104 is configured to substantially maintain leadlet 108 in a stowage configuration. IMD 104 may be configured to substantially maintain leadlet 108 in the stowage configuration until proximal body portion 120 is caused to rotate (e.g., by a clinician) relative to distal body portion 122. Leadlet 108 and/or device body 106 may be configured such that leadlet 108 is positioned within the outer boundary B defined by device body 106 when leadlet 108 is in the stowage configuration. IMD 104 may be configured such that rotation of proximal body portion 120 relative to distal body portion 122 (e.g., in the first rotational direction W1) causes leadlet 108 (e.g., leadlet distal end 126) to pass through and/or cross the outer boundary B and increase the extension length LE (e.g., by passing through leadlet access 130). IMD 104 may be configured such that rotation of proximal body portion 120 relative to distal body portion 22 (e.g., in the second rotational direction) causes leadlet 108 (e.g., leadlet distal end 126) to substantially retract back to within the outer boundary B (e.g., by passing through leadlet access 130). Hence, IMD 104 may be configured such that leadlet 108 may be extended beyond the outer boundary B from a stowage configuration, and subsequently retracted back within the outer boundary B to substantially re-establish the stowage configuration. Thus, leadlet 108 may be substantially maintained in the stowage configuration during delivery of IMD 104 through vasculature to heart 102, deployed from the stowage condition to position leadlet electrode 116 within tissues of heart 102, and/or re-established in the stowage configuration in the event IMD 104 is retrieved through vasculature from heart 102.

In examples, device body 106 defines a leadlet stowage space 144 configured to substantially surround leadlet 108 when leadlet 108 is in the stowage configuration. Leadlet stowage space 144 may be volume defined within the outer boundary B of device body 106. Leadlet access 130 may be an opening to leadlet stowage space 144. In examples, IMD 104 is configured such that a rotation of proximal body portion 120 relative to distal body portion 122 (e.g., in the first rotational direction W1) causes leadlet distal end 126 to emerge from leadlet stowage space 144 via leadlet access 130. IMD 104 may be configured such that a rotation of proximal body portion 120 relative to distal body portion 122 (e.g., in the second rotational direction W2) causes leadlet distal end 126 to displace from a position outside of outer boundary B to a position within leadlet stowage space 144 via leadlet access 130.

Device body 106 may be configured to define leadlet stowage space 144 between proximal body portion 120 and distal body portion 122. In examples, device body 106 is configured to define leadlet stowage space 144 between axial portion 138 and distal body portion 122 when distal body portion 122 at least partially surrounds axial portion 138. In some examples, leadlet 108 is configured to substantially coil around longitudinal axis L (FIG. 3) when leadlet 108 is positioned within leadlet stowage space 144. Leadlet 108 may be configured to substantially coil around axial portion 138 when leadlet 108 is positioned within leadlet stowage space 144. IMD 104 may be configured such that rotation of proximal body portion 120 relative to distal body portion 122 (e.g., in the first rotational direction W1) causes leadlet 108 to substantially spool out of leadlet stowage space 144 through leadlet access 130 when leadlet 108 is substantially coiled around longitudinal axis L. IMD 104 may be configured such that rotation of proximal body portion 120 relative to distal body portion 122 (e.g., in the second rotational direction W2) causes leadlet 108 to retract toward device body 106 and substantially coil around longitudinal axis L within leadlet stowage space 144.

Fixation mechanism 124 is configured to engage tissue at a target site (e.g., target site 112 (FIG. 1)) to secure IMD 104 to the tissue. Fixation mechanism 124 may be configured to substantially secure distal body portion 122 in a position relative to the tissues at the target site, such that a torque applied to proximal body portion 120 causes proximal body portion 120 to rotate around longitudinal axis L relative to distal body portion 122. In examples, fixation mechanism 124 is configured to be rotationally stationary with respect to distal body portion 122. Fixation mechanism 124 may include, for example, one or more elongated tines such as fixation tine 148 configured to substantially maintain an orientation of distal body portion 122 with respect to a target site (e.g., target site 112). Fixation mechanism 124 may include fixation tines of any shape, including helically-shaped fixation tines. In examples, fixation mechanism 124 is configured to substantially maintain contact between second electrode 121 and tissues within a target site when fixation mechanism 124 engages the tissue. Fixation mechanism 124 may be configured to position within the cup section of delivery catheter 110 (FIG. 1) when IMD 104 is positioned within the cup section, with one or more tines such as tine 148 resiliently biased to deploy outward to grasp tissue when delivery catheter 110 is proximally withdrawn (e.g., by the clinician).

As an example, FIG. 4A illustrates an example IMD 204 positioned within a cup section 250 of a delivery catheter 210. FIG. 4B illustrates IMD 204 with delivery catheter 210 and cup section 250 proximally displaced from IMD 204. Delivery catheter 210 is illustrated as a cross-section with a cutting plane parallel to the page. Delivery catheter 210 is an example of delivery catheter 110. IMD 204 is an example of IMD 104. IMD 204 further includes device body 206, proximal body portion 220, distal body portion 222, second electrode 221, return electrode 223, fixation mechanism 224 with fixation tine 248, and leadlet access 230, which may be configured individually and in relation to each other in the same manner as that described for like-named components of IMD 104.

Cup section 250 may define a lumen 252 configured to at least circumferentially surround IMD 204, such that delivery catheter 210 may deliver IMD 204 to heart 102 (FIG. 1). In examples, cup section 250 includes an inner wall 253 defining lumen 252. Cup section 250 may define a lumen opening 254 opening to lumen 252 at a distal end 256 of cup section 250 ("cup distal end 256") configured such that fixation mechanism 224 and device body 206 may pass therethrough. Fixation mechanism 224 may be configured to engage tissue (e.g., within target site 112 (FIG. 1)) as fixation mechanism 224 passes through lumen opening 254. In examples, fixation mechanism 224 (e.g., fixation tine 248) is configured to extend distally from distal body portion 222 when IMD 204 is positioned within cup section 250. Fixation mechanism 224 may be configured to penetrate tissues as fixation mechanism 224 passes through lumen opening 254 in order to engage the tissues. For example, a portion of fixation mechanism 224 (e.g., fixation tine 248) may be resiliently biased to expand outward as fixation mechanism 224 passes through lumen opening 254, in order to aid in grasping the tissue. Cup section 250 may be configured to radially constrain fixation mechanism 224 (e.g., fixation tine 248) when fixation mechanism 224 is proximal to lumen opening 254.

In examples, fixation tine 248 includes a fixed end 258 mechanically supported by distal body portion 222 and a free end 260 opposite fixed end 258. In examples, free end 260 is configured to penetrate tissue. Fixation tine 248 may be biased so that at least some portion of fixation tine 248 expands radially as fixation tine 248 passes through lumen opening 254. Fixation tine 248 may be biased to drive free end 260 radially outward from longitudinal axis L of IMD 204 as free end 260 passes through lumen opening 254, as illustrated in FIG. 4B. The biasing tending to drive free end 260 radially outward as fixation tine 248 extends through lumen opening 254 may cause fixation tine 248 to substantially grasp tissue and more securely attach distal body portion 222 to tissues (e.g., within heart 102). Free end 260 may pierce the tissue and may act to pull IMD 204 toward a target site as fixation tine 248 elastically bends or curves radially outward. Fixation mechanism 224 may include any number of fixation tines, which may be configured similarly to fixation tine 248.

The biasing of fixation tine 248 tending to drive free end 260 radially outward may cause fixation tine 248 to assume any general shape. In some examples, the biasing of fixation tine 248 tends to cause fixation tine 248 to position such that free end 260 establishes a position distal to a midpoint M between fixed end 258 and free end 260 (e.g., as depicted in FIG. 4B). In some examples, the biasing of fixation tine 248 tends to cause fixation tine 248 to position such that free end 260 establishes a position proximal to midpoint M. Fixation tine 248 may be formed to have a preset shape and may be formed using any suitable material. In examples, fixation tine 248 comprises a nickel-titanium alloy such as Nitinol.

In some examples, fixation tine 248 may be configured to substantially maintain a delivery configuration where free end 260 is distal to fixed end 258 and distal to midpoint M (e.g., as depicted in FIG. 4A). For example, fixation tine 248 may be configured to substantially maintain the delivery configuration when free end 260 is constrained from outward radial motion by inner wall 253. Cup section 250 may be configured to substantially maintain fixation tine 248 in the delivery configuration as delivery catheter 210 translates through vasculature to deliver IMD 204 to heart 102. Substantially maintaining free end 260 distal to midpoint M (e.g., in the delivery configuration) may facilitate the penetration of tissue by free end 260 when fixation tine 248 passes through lumen opening 254 of delivery catheter 18.

Fixation tine 248 may refer to any structure that is capable of securing a lead or leadless implantable medical device to a location within the heart. In some examples, a tine (e.g., fixation tine 248) may be composed of a shape-memory allow that allows deformation along the length of the tine. A tine may be substantially flat along the length of the tine. In other examples, a tine may substantially define a helix and/or helical member.

In examples, IMD 204 is configured to receive a force imparted by a delivery tether 262. Delivery tether 262 may be configured to impart a force to cause IMD 204 to translate in a proximal or distal direction. For example, delivery tether 262 may be configured to impart a force to cause IMD 204 to pass through lumen opening 254 to at least partially exit cup section 250. In examples, delivery tether 262 is configured to impart a torque around longitudinal axis L to IMD 204 to cause some portion of IMD 204 (e.g., proximal body portion 220) to rotate around longitudinal axis L. Delivery tether 262 may be configured to impart a torque proximal body portion 220 to cause proximal body portion 220 to rotate relative to distal body portion 222 (e.g., when fixation mechanism 224 engages tissue within, for example, target site 112 (FIG. 1)). In examples, delivery tether 262 is configured to mechanically engage IMD 204 (e.g., proximal body portion 220) to impart a force and/or torque to IMD 204.

Figure 5B:
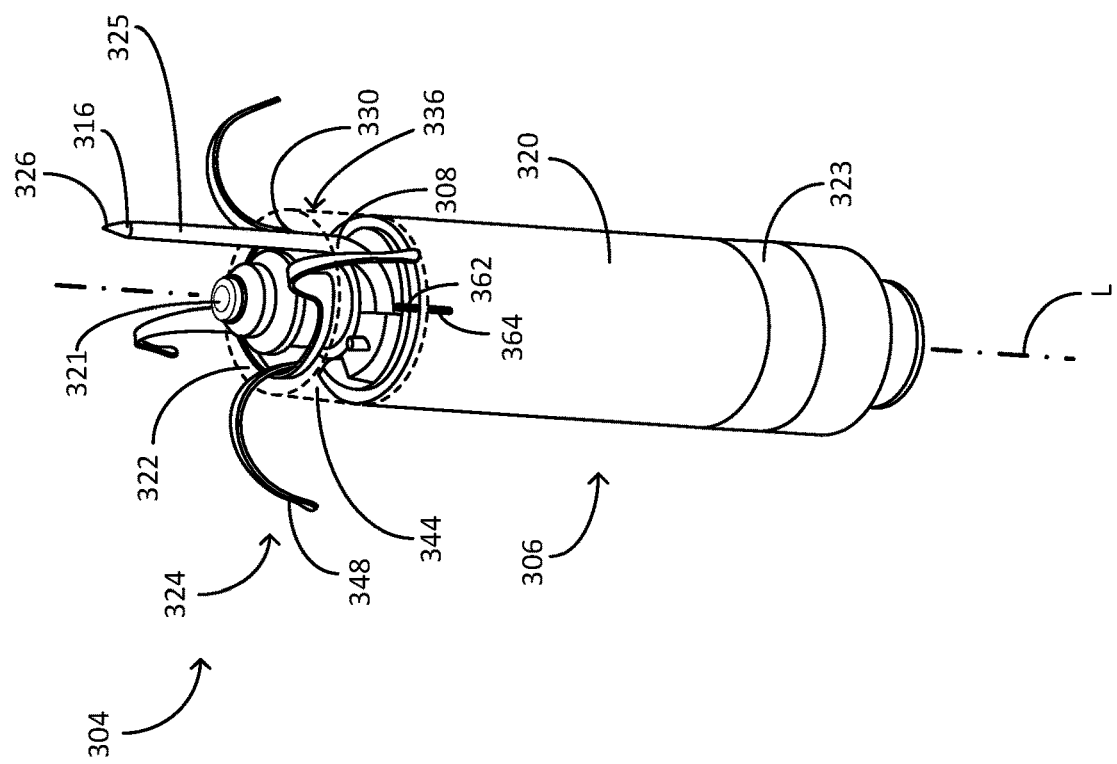
FIG. 5B is a perspective view of the implantable medical device of FIG. 5A with the leadlet extending from the leadlet stowage space.
Figure 5A:
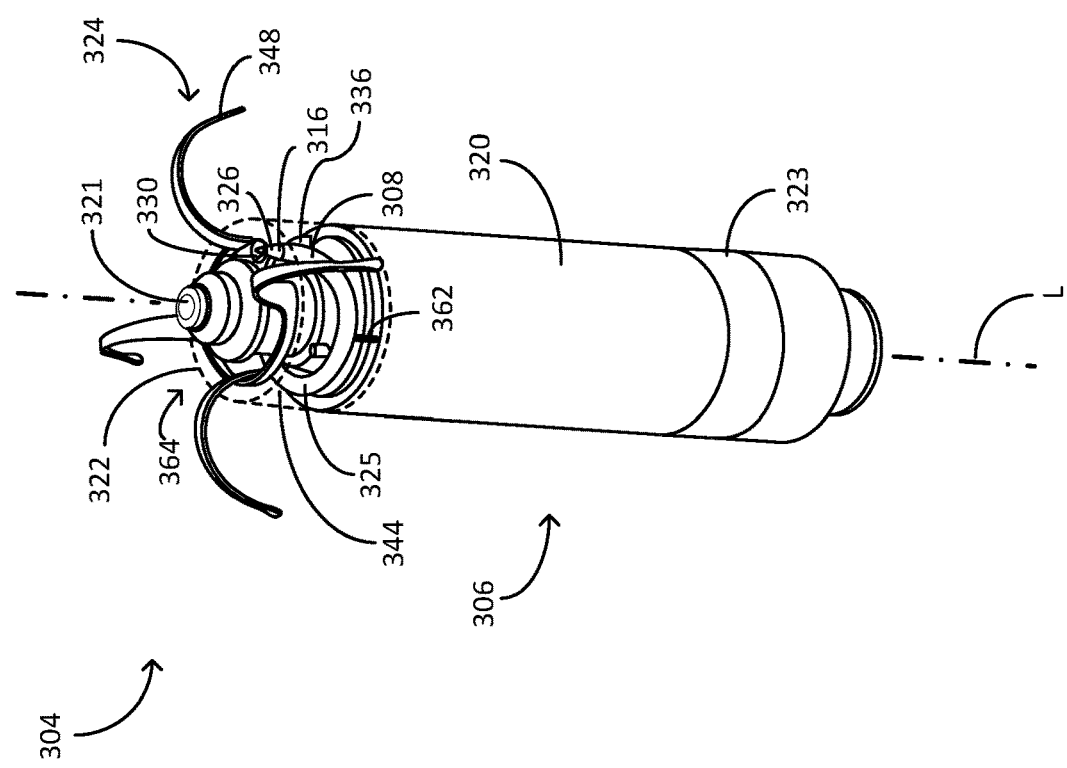
FIG. 5A is a perspective view of an implantable medical device with a leadlet in a leadlet stowage space.

FIG. 5A and FIG. 5B illustrate an example IMD 304 configured to cause a leadlet 308 to extend from a device body 306 in a direction substantially parallel to longitudinal axis L. Device body 306 includes proximal body portion 320 and a distal body portion 322, with distal body portion 322 shown as a transparent component for illustration. IMD 304, leadlet 308, device body 306, proximal body portion 320, and distal body portion 322 are examples of IMD 104, 204, leadlet 108, 208, device body 106, 206, proximal body portion 120, 220, and distal body portion 122, 222 respectively. IMD 304 further includes leadlet electrode 316, second electrode 321, return electrode 323, fixation mechanism 324 with fixation tine 348, leadlet body 325, leadlet distal end 326, leadlet access 330, directing structure 336, and leadlet stowage space 344, which may be configured individually and in relation to each other in the same manner as that described for like-named components of IMD 104 and/or IMD 204.

FIG. 5A illustrates leadlet 308 in a stowage configuration within leadlet stowage space 344 defined between distal body portion 322 and proximal body portion 320. FIG. 5B illustrates IMD 304 with proximal body portion 320 having rotated around longitudinal axis L to cause leadlet 308 to extend through leadlet access 330. IMD 304 includes directing structure 336 configured to cause leadlet 308 to extend in a direction substantially parallel to longitudinal axis L when a force is exerted on leadlet body 325 (e.g., by proximal body portion 320). FIG. 5B illustrates leadlet 308 extending in the direction substantially parallel to longitudinal axis L. Directing structure 336 may be defined by some portion of proximal body portion 320 and/or distal body portion 322. Leadlet access 330 may be configured such that, when directing structure 336 causes leadlet 308 to extend in a direction substantially parallel to longitudinal axis L, leadlet 308 passes through leadlet access 330.

In examples, distal body portion 322 includes a marker 362 ("distal marker 362") and proximal body portion 320 includes a marker 364 ("proximal marker 364"). Distal marker 362 may be configured to visually align with proximal marker 364 (as illustrated in FIG. 5B) when proximal body portion 320 establishes a particular rotational orientation with respect to distal body portion 322. Distal marker 362 and proximal marker 364 may be configured such that a displacement between distal marker 362 and proximal marker 364 is indicative of a rotational position of proximal body portion 320 relative to distal body portion 322. In examples, distal marker 362 and proximal marker 364 are configured such that a displacement between distal marker 362 and proximal marker 364 is indicative of the extension length of leadlet 308 (e.g., the extension length LE (FIG. 2B)). In some examples, distal marker 362 and proximal marker 364 are configured to align when proximal body portion 320 reaches a limit of rotation relative to distal body portion 322. For example, distal marker 362 and proximal marker 364 may be configured to align when proximal body portion 320 reaches a rotational limit such that proximal body portion 320 is prevented from further rotation in the first rotational direction W1 (FIG. 2B) relative to distal body portion 322. Distal marker 362 and proximal marker 364 may be configured to align when proximal body portion 320 reaches a rotational limit such that proximal body portion 320 is prevented from further rotation in the second rotational direction W2 (FIG. 2B) relative to distal body portion 322. IMD 304 may include any number of distal markers and/or proximal markers, which may be configured to indicate any rotational orientation of proximal body portion 320 with respect to distal body portion 322.

In examples, distal marker 362 and/or proximal marker 364 are configured to be visible on an imaging display of an imaging apparatus when IMD 304 is within a patient and imaged by the imaging apparatus. The imaging apparatus may be any type of imaging apparatus configured to image, or provide images of, IMD 304 within a patient. For example, the imaging apparatus may be configured to capture images of IMD 304 within a patient using one or more image modalities such as x-ray images, fluoroscopy, ultrasound, computed tomography (CT), magnetic resonance imaging (MRI), and/or others. Hence, distal marker 362 and/or proximal marker 364 may be configured such that clinician may view an image of distal marker 362 and/or proximal marker 364 on the imaging display to estimate the relative orientation of proximal body portion 320 with respect to distal body portion 322.

As discussed, medical system 100 (e.g., IMD 104, 204, 304, or another external device) may include circuitry 118 configured to deliver therapy to and/or sense cardiac signals from heart 102 (FIG. 1) using leadlet electrode 116, 216, 316, return electrode 123, 223, 323, and/or second electrode 121, 221, 321. Circuitry 118 may be operably coupled to leadlet electrode 116, 216, 316, return electrode 123, 223, 323, and/or second electrode 121, 221, 321 via one or more conductors. Circuitry 118 may be configured to transmit therapy signals using leadlet electrode 116, 216, 316, return electrode 123, 223, 323, and/or second electrode 121, 221, 321, and may be configured to receive data representative of heart 102 from leadlet electrode 116, 216, 316, return electrode 123, 223, 323, and/or second electrode 121, 221, 321. In examples, circuitry 118 includes one or more processors that are configured to implement functionality and/or process instructions stored in a storage device. Circuitry 118 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Circuitry 118 may include any suitable structure, whether in hardware, software, firmware, or any combination thereof, to perform the functions ascribed herein to the circuitry.

In examples, circuitry 118 is located within a housing of IMD 104, 204, 304. In other examples, circuitry 118 is located within another device or group of devices external to IMD 104, 204, 304 (e.g., within a device or group of devices not illustrated in FIG. 1). As such, techniques and capabilities attributed herein to circuitry 118 may be attributed to any combination of IMD 104, 204, 304 and other devices that are not illustrated in FIG. 1. Hence, medical system 100 (FIG. 1) may represent a system wherein portions are configured to be implanted within a patient and/or configured to be extracorporeal to a patient, and may include any fixed or mobile computer system (e.g., a controller, a microcontroller, a personal computer, minicomputer, tablet computer, etc.), and may be generally described as including substantially all or some portion of circuitry 118.

Figure 6:
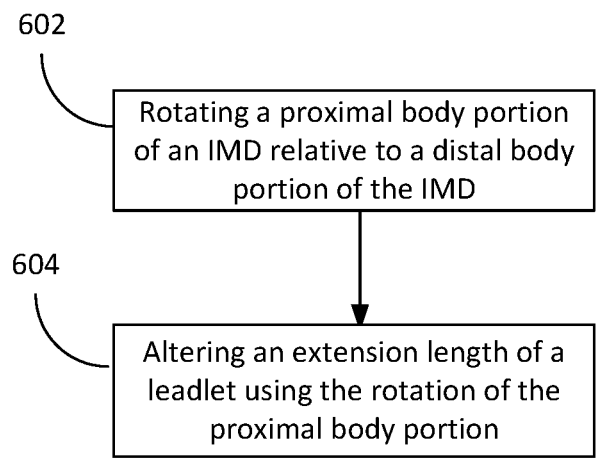
FIG. 6 illustrates an example technique for using the example implantable medical device.

A technique for implanting an IMD 104, 204, 304 within a heart 102 is illustrated in FIG. 6. Although the technique is described mainly with reference to IMD 104, 204, 304, FIGS. 1-5B, the technique may be applied to other medical devices in other examples.

The technique includes rotating a proximal body portion 120, 220, 320 relative to a distal body portion 122, 222, 322 (602). The technique may include securing distal body portion 122, 222, 322 to tissue within target site 112 using fixation mechanism 124, 224, 324. In examples, proximal body portion 120, 220, 320 rotates relative to distal body portion 122, 222, 322 as fixation mechanism 124, 224, 324 substantially maintains distal body portion 122, 222, 322 substantially stationary with respect to the tissue within target site 112.

In examples, the technique includes guiding IMD 104, 204, 304 through vasculature of a patient to target site 112 within heart 102 using delivery catheter 110, 210. Delivery catheter 110, 210 may substantially retain IMD 104, 204, 304 within lumen 252 of cup section 250 as delivery catheter 110, 210 guides IMD 104, 204, 304 to target site 112. Delivery catheter 110, 210 may retain fixation mechanism 124, 224, 324 in a delivery configuration within cup section 250 using inner wall 253. In examples, the technique includes exerting a distal force on IMD 104, 204, 304 to cause IMD 104, 204, 304 to pass through lumen opening 254 when, for example, delivery catheter 110, 210 positions IMD 104, 204, 304 at or in the vicinity of target site 112. Fixation tine 148, 248 may expand radially outward from longitudinal axis L of IMD 104, 204, 304 when fixation mechanism 124, 224, 324 passes through lumen opening 254 to secure IMD 104, 204, 304 to target site 112.

The technique includes deploying leadlet 108, 208, 308 to extend over an extension length LE in a direction away from device body 106, 206, 306. The technique may include exerting a force on leadlet 108, 208, 308 to cause leadlet 108, 208, 308 to extend away from device body 106, 206, 306. In examples, the technique includes using the rotation of proximal body portion 120, 220, 320 relative to distal body portion 122, 222, 322 to exert the force on leadlet 108, 208, 308. In examples, the technique includes exerting the force on leadlet 108, 208, 308 using an elongated body such as a stylet. Leadlet distal end 126, 326 may penetrate tissues at or in the vicinity of target site 112 when leadlet 108, 208, 308 deploys to extend over the extension length LE. Leadlet 108, 208, 308 may pass through leadlet access 130, 230, 330 when leadlet 108, 208, 308 deploys to extend over the extension length LE.

The technique may include altering the extension length LE defined by leadlet 108, 208, 308 using the rotation of proximal body portion 120, 220, 320 relative to distal body portion 122, 222, 322 (604). Proximal body portion 120, 220, 320 may rotate relative to distal body portion 122, 222, 322 in the first rotational direction W1 and/or in the second rotational direction W2. In examples, the rotation of proximal body portion 120, 220, 320 relative to distal body portion 122, 222, 322 causes the extension length LE to increase. In examples, the rotation of proximal body portion 120, 220, 320 relative to distal body portion 122, 222, 322 causes the extension length LE to decrease. In examples, the technique includes rotating proximal body portion 120, 220, 320 relative to distal body portion 122, 222, 322 to align distal marker 362 and proximal marker 364.

The technique may include retaining leadlet 108, 208, 308 within leadlet stowage space 144, 244 as delivery catheter 110, 210 transports IMD 104, 204, 304 through vasculature of a patient. Leadlet 108, 208, 308 may deploy from leadlet stowage space 144, 244 when leadlet 108, 208, 308 establishes the extension length LE. In examples, the rotation of proximal body portion 120, 220, 320 relative to distal body portion 122, 222, 322 causes leadlet 108, 208, 308 to deploy from the stowage configuration. In examples, the rotation of proximal body portion 120, 220, 320 relative to distal body portion 122, 222, 322 causes leadlet 108, 208, 308 to retract toward device body 106, 206, 306 and substantially re-establish the stowage configuration.

The rotation of proximal body portion 120, 220, 320 relative to distal body portion 122, 222, 322 may cause leadlet 108, 208, 308 to substantially establish the extension length LE in a specific direction relative to the longitudinal axis L. In examples, leadlet 108, 208, 308 establishes the extension length LE in a direction substantially perpendicular to longitudinal axis L. In examples, leadlet 108, 208, 308 establishes the extension length LE in a direction substantially parallel to longitudinal axis L. Directing structure 136 may engage leadlet 108, 208, 308 to cause leadlet 108, 208, 308 to establish the extension length LE in the specific direction relative to longitudinal axis L.

The technique may include causing second electrode 121, 221, 321 to contact tissues of heart 102 when fixation mechanism 124, 224, 324 secures IMD 104, 204, 304 to target site 112. The technique may include delivering therapy to and/or sensing cardiac signals from heart 102 using circuitry 118. Circuitry 118 may deliver therapy and/or sense cardiac signals using leadlet electrode 116, 216, 316, return electrode 123, 223, 323, and/or second electrode 121, 221, 321. Circuitry 118 may deliver therapy and/or sense cardiac signals when leadlet 108, 208, 308 establishes the extension length LE. Circuitry 118 may deliver therapy and/or sense cardiac signals when fixation mechanism 124, 224, 324 secures distal body portion 122, 222, 322 to tissue at or in the vicinity of target site 112.

In illustrative aspect A1, an implantable medical device configured to deliver pacing therapy, the implantable medical device including: a device body configured to position within a heart, where the device body includes a proximal body portion and a distal body portion and defines a longitudinal axis extending through the proximal body portion and the distal body portion, the proximal body portion is configured to rotate around the longitudinal axis relative to distal body portion; and a leadlet mechanically coupled to the device body, where the leadlet mechanically supports an electrode, and where in response to the proximal body portion rotating relative to the distal body portion, the device body is configured to alter an extension length of the leadlet.

In illustrative aspect A2, the implantable medical device of any A aspect, further including a fixation mechanism attached to the distal body portion, where the fixation mechanism is configured to attach to tissues of the heart.

In illustrative aspect A3, the implantable medical lead of any A aspect, where the fixation mechanism includes one or more tines, where a tine includes a fixed end and a free end, where the fixed end is mechanically coupled to the distal body portion, and where the tine is biased to drive the free end radially outward from the longitudinal axis.

In illustrative aspect A4, the implantable medical device of any A aspect, further including a second electrode mechanically coupled to the device body, where the second electrode is configured to contact tissues of the heart when the fixation mechanism attaches to tissues of the heart.

In illustrative aspect A5, the implantable medical lead of aspect A4, where the second electrode is rotationally coupled to the proximal body portion.

In illustrative aspect A6, the implantable medical lead of aspect A4 or A5, further including a second leadlet mechanically supported by the device body, where the second leadlet mechanically supports the second electrode.

In illustrative aspect A7, the implantable medical device of any A aspect, where the distal body portion is configured to at least one of increase the extension length of the leadlet when the proximal body portion rotates relative to the distal body portion or decrease the extension length of the leadlet when the proximal body portion rotates relative to the distal body portion.

In illustrative aspect A8, the implantable medical device of any A aspect, where distal body portion is configured to cause the leadlet to extend in a direction substantially perpendicular to the longitudinal axis when the proximal body portion rotates relative to distal body portion.

In illustrative aspect A9, the implantable medical device of any A aspect, where distal body portion is configured to cause the leadlet to extend in a direction substantially parallel to the longitudinal axis when the proximal body portion rotates relative to distal body portion.

In illustrative aspect A10, the implantable medical device of any A aspect, where distal body portion is configured to insert into a coronary sinus of the heart.

In illustrative aspect A11, the implantable medical device of any A aspect, where: the leadlet includes a leadlet body extending to a leadlet distal end; and the leadlet body is configured to transmit a force to the leadlet distal end to cause the leadlet distal end to penetrate tissues of the heart when the proximal body portion rotates relative to distal body portion.

In illustrative aspect A12, the implantable medical device of any A aspect, where the leadlet includes a leadlet body extending to a leadlet distal end, and where the leadlet is biased to cause the leadlet body to assume a substantially straight orientation when the leadlet extends from the device body.

In illustrative aspect A13, the implantable medical device of any A aspect, where: the leadlet includes a leadlet body extending to a leadlet distal end; the leadlet distal end includes a bearing structure configured to receive an elongated body; and the bearing structure is configured to transfer a force from the elongated body to the leadlet distal end to cause the distal end to penetrate tissues of the heart.

In illustrative aspect A14, the implantable medical device of any A aspect, further including circuitry mechanically supported within a volume of the device body, where the circuitry is configured to provide therapy signals to the heart, and where the electrode is operably connected to the circuitry.

In illustrative aspect A15, the implantable medical device of aspect A14, where the device body mechanically supports a return electrode operably connected to the circuitry.

In illustrative aspect A16, the implantable medical device of any A aspect, where: the distal body portion includes a distal marker visible on an imaging modality when implantable medical device is within a patient; the proximal body portion includes a proximal marker visible on the imaging modality when the implantable medical device is within the patient; and the distal marker and the proximal marker are configured to substantially align when the distal body portion has a specific rotational orientation relative to the proximal body portion.

In illustrative aspect A17, the implantable medical device of any A aspect, where the leadlet is attached to the distal body portion.

In illustrative aspect A18, the implantable medical device of any A aspect, where the device body includes an axial portion surrounding the longitudinal axis and rotationally coupled to the proximal body portion, where the axial portion is configured to rotate within an inner perimeter defined by the distal body portion.

In illustrative aspect A19, the implantable medical device of aspect A18, where the axial portion and the distal body portion define a leadlet stowage space between the axial portion and the distal body portion, and where the leadlet is configured to deploy from the leadlet stowage space when the proximal body portion rotates relative to distal body portion.

In illustrative aspect A20, the implantable medical device of aspect A18 or A19, where the distal body portion substantially surrounds the axial portion.

In illustrative aspect A21, the implantable medical device of any A aspect, where the distal body portion is configured such that the leadlet extends through a leadlet access of the distal body portion when the proximal body portion rotates relative to distal body portion.

In illustrative aspect A22, the implantable medical device of any A aspect, where the proximal body portion mechanically supports the distal body portion such that when the distal body portion exerts an action force parallel to the longitudinal axis on the proximal body portion, the proximal body portion exerts a reaction force opposite the action force on the distal body portion.

In illustrative aspect A23, the implantable medical device of any A aspect, where the leadlet body is configured to alter a displacement between the electrode and the leadlet body when the rotation of the proximal body portion relative to the distal body portion alters the extension length of the leadlet.

In illustrative aspect A24, the implantable medical device of any A aspect, where the leadlet is in a stowage configuration.

In illustrative aspect A25, the implantable medical device of any A aspect, where the leadlet is positioned within an outer boundary defined by the device body when the leadlet is in the stowage configuration.

In illustrative aspect A26, the implantable medical device of any A aspect, where the leadlet in a deployment configuration, where in the deployment configuration the leadlet extends over the extension length from the device body.

In illustrative aspect B1, a method, includes rotating a proximal body portion of a device body around a longitudinal axis of the implantable device and relative to a distal body portion of the device body, where the device body is configured to position within a heart and includes an implantable medical device; and altering an extension length of a leadlet attached to the device body and extending from the device body using the rotation of the proximal body portion relative to the distal body portion, where the leadlet mechanically supports an electrode.

In illustrative aspect B2, the method of any B aspect, further including attaching the device body to tissue of the heart using a fixation mechanism configured to attach to tissues of the heart.

In illustrative aspect B3, the method of any B aspect, where attaching the device body to tissues of the heart using the fixation mechanism includes attaching the device body to tissues of the heart using one or more tines.

In illustrative aspect B4, the method of any B aspect, further including a contacting a second electrode with tissues of the heart when the fixation mechanism attaches to tissues of the heart.

In illustrative aspect B5, the method of aspect B4, further including rotating the second electrode relative to the distal body portion when the proximal body portion rotates relative to the distal body portion.

In illustrative aspect B6, the method of any B aspect, further including increasing the extension length of the leadlet when the proximal body portion rotates relative to the distal body portion.

In illustrative aspect B7, the method of any B aspect, further including decreasing the extension length of the leadlet when the proximal body portion rotates relative to the distal body portion.

In illustrative aspect B8, the method of any B aspect, further including extending the leadlet in a direction substantially perpendicular to the longitudinal axis when the proximal body portion rotates relative to distal body portion.

In illustrative aspect B9, the method of any B aspect, further including extending the leadlet in a direction substantially parallel to the longitudinal axis when the proximal body portion rotates relative to distal body portion.

In illustrative aspect B10, the method of any B aspect, further including inserting the distal body portion into a coronary sinus of the heart.

In illustrative aspect B11, the method of any B aspect, further including: transmitting a force to a distal end of the leadlet when the proximal body portion rotates relative to distal body portion; and penetrating tissues of the heart with the distal end using the transmitted force.

In illustrative aspect B12, the method of any B aspect, further including: transmitting a force from an elongated body to a distal end of the leadlet; and penetrating tissues of the heart with the distal end using the transmitted force.

In illustrative aspect B13, the method of any B aspect, further including providing therapy signals to the electrode from circuitry mechanically supported within a volume of the device body.

In illustrative aspect B14, the method of any B aspect, further including rotating a proximal marker on the proximal body portion relative to a distal marker on the distal body portion when the proximal body portion rotates relative to the distal body portion.

In illustrative aspect B15, the method of any B aspect, further including rotating an axial portion of the device body surrounded by the distal body portion relative to the distal body portion when the proximal body portion rotates relative to the distal body portion.

In illustrative aspect B16, the method of aspect B15, further including deploying the leadlet from a leadlet stowage space defined between the axial portion and the distal body portion.

In illustrative aspect B17, the method of any B aspect, further including extending the leadlet through a leadlet access of the distal body portion when the proximal body portion rotates relative to distal body portion.

In illustrative aspect B18, the method of any B aspect, further including altering a displacement between the electrode and the leadlet body when the proximal body portion rotates relative to the distal body portion.

In illustrative aspect B19, the method of any B aspect, further including rotating the proximal body portion relative to the distal body portion of the device body to place the leadlet in a stowage configuration.

In illustrative aspect B20, the method of any B aspect, where placing the leadlet in the stowage configuration includes positioning the leadlet within an outer boundary defined by the device body.

In illustrative aspect B21, the method of any B aspect, further including penetrating tissues with a distal end of the leadlet when the rotation alters the extension length of the leadlet.

In illustrative aspect B22, the method of any B aspect, further including contacting a surface of a tissue with a distal end of the leadlet when the rotation alters the extension length of the leadlet.

In illustrative aspect C1, an implantable medical device configured to deliver pacing therapy including: a device body configured to position within a heart, where the device body includes a proximal body portion and a distal body portion and defines a longitudinal axis extending through the proximal body portion and the distal body portion, and where the proximal body portion is configured to rotate around the longitudinal axis relative to distal body portion; a fixation mechanism attached to the distal body portion, where the fixation mechanism is configured to attach the implantable medical device to tissues of the heart; and a leadlet mechanically coupled to the device body, where: the leadlet mechanically supports an electrode configured to deliver pacing therapy to a portion of a heart; in response to the proximal body portion rotating relative to the distal body portion, the device body is configured to alter an extension length of the leadlet; and the leadlet is configured to define a deployment configuration and a stowage configuration, where in the stowage configuration the leadlet is positioned within an outer boundary defined by the device body, and where the in the deployment configuration the leadlet is configured to extend over the extension length from the device body.

In illustrative aspect C2, the implantable medical device of any C aspect, further including a fixation mechanism attached to the distal body portion, where the fixation mechanism is configured to attach to tissues of the heart.

In illustrative aspect C3, the implantable medical device of any C aspect, further including a second electrode mechanically coupled to the device body, where the second electrode is configured to contact tissues of the heart when the fixation mechanism attaches to tissues of the heart.

In illustrative aspect C4, the implantable medical device of aspect C3, where the second electrode is rotationally coupled to the proximal body portion.

In illustrative aspect C5, the implantable medical device of any C aspect, further including a second leadlet mechanically supported by the device body, where the second leadlet mechanically supports the second electrode.

In illustrative aspect C6, the implantable medical device of any C aspect, where the distal body portion is configured to at least one of increase the extension length of the leadlet when the proximal body portion rotates relative to the distal body portion or decrease the extension length of the leadlet when the proximal body portion rotates relative to the distal body portion.

In illustrative aspect C7, the implantable medical device of any C aspect, where distal body portion is configured to cause the leadlet to extend in a direction substantially perpendicular to the longitudinal axis when the proximal body portion rotates relative to distal body portion.

In illustrative aspect C8, the implantable medical device of any C aspect, where distal body portion is configured to cause the leadlet to extend in a direction substantially parallel to the longitudinal axis when the proximal body portion rotates relative to distal body portion.

In illustrative aspect C9, the implantable medical device of any C aspect, where distal body portion is configured to insert into a coronary sinus of the heart.

In illustrative aspect C10, the implantable medical device of any C aspect, where: the leadlet includes a leadlet body extending to a leadlet distal end; and the leadlet body is configured to transmit a force to the leadlet distal end to cause the leadlet distal end to penetrate tissues of the heart when the proximal body portion rotates relative to distal body portion.

In illustrative aspect C11, the implantable medical device of any C aspect, where the leadlet includes a leadlet body extending to a leadlet distal end, and where the leadlet is biased to cause the leadlet body to assume a substantially straight orientation when the leadlet extends from the device body.

In illustrative aspect C12, the implantable medical device of any C aspect, where: the leadlet includes a leadlet body extending to a leadlet distal end, the leadlet distal end includes a bearing structure configured to receive an elongated body; and the bearing structure is configured to transfer a force from the elongated body to the leadlet distal end to cause the distal end to penetrate tissues of the heart.

In illustrative aspect C13, the implantable medical device of any C aspect, further including circuitry mechanically supported within a volume of the device body, where the circuitry is configured to provide therapy signals to the heart, and where the electrode is operably connected to the circuitry.

In illustrative aspect C14, the implantable medical device of aspect C13, where the device body mechanically supports a return electrode operably connected to the circuitry.

In illustrative aspect C15, the implantable medical device of any C aspect, where the distal body portion includes a distal marker visible on an imaging modality when implantable medical device is within a patient, the proximal body portion includes a proximal marker visible on the imaging modality when the implantable medical device is within the patient, and the distal marker and the proximal marker are configured to substantially align when the distal body portion has a specific rotational orientation relative to the proximal body portion.

In illustrative aspect C16, the implantable medical device of any C aspect, where the leadlet is attached to the proximal body portion.

In illustrative aspect C17, the implantable medical device of any C aspect, where the device body includes an axial portion surrounding the longitudinal axis and rotationally coupled to the proximal body portion, where the axial portion is configured to rotate within an inner perimeter defined by the distal body portion.

In illustrative aspect C18, the implantable medical device of aspect C17, where the axial portion and the distal body portion define a leadlet stowage space between the axial portion and the distal body portion, and where the leadlet is configured to deploy from the leadlet stowage space when the proximal body portion rotates relative to distal body portion.

In illustrative aspect C19, the implantable medical device of any C aspect, where the distal body portion is configured such that the leadlet extends through a leadlet access of the distal body portion when the proximal body portion rotates relative to distal body portion.

In illustrative aspect C20, the implantable medical device of any C aspect, where the proximal body portion mechanically supports the distal body portion such that when the distal body portion exerts an action force parallel to the longitudinal axis on the proximal body portion, the proximal body portion exerts a reaction force opposite the action force on the distal body portion.

In illustrative aspect C21, the implantable medical device of any C aspect, where the leadlet body is configured to alter a displacement between the electrode and the leadlet body when the rotation of the proximal body portion relative to the distal body portion alters the extension length of the leadlet.

Various examples of the disclosure have been described. Any combination of the described systems, operations, or functions is contemplated. These and other examples are within the scope of the following claims.

What is claimed is:

1. An implantable medical device configured to deliver therapy, the implantable medical device comprising:
    a device body configured to position within a heart, wherein the device body comprises a proximal body portion and a distal body portion and defines a longitudinal axis extending through the proximal body portion and the distal body portion, wherein the proximal body portion is configured to rotate around the longitudinal axis relative to distal body portion, wherein the device body mechanically supports circuitry configured to deliver the therapy to the heart, wherein the device body is configured to position the circuitry within the heart when the device body positions within the heart, and wherein the device body includes an axial portion surrounding the longitudinal axis and rotationally coupled to the proximal body portion, wherein the axial portion is configured to rotate within an inner perimeter defined by the distal body portion, the axial portion and the distal body portion defining a leadlet stowage space between the axial portion and the distal body portion; and
    a leadlet mechanically coupled to the device body, wherein the leadlet mechanically supports an electrode, and wherein the leadlet is configured to deploy from the leadlet stowage space when the proximal body portion rotates relative to distal body portion.

2. The implantable medical device of claim 1, further comprising a fixation mechanism attached to the distal body portion, wherein the fixation mechanism is configured to attach to tissues of the heart.

3. The implantable medical device of claim 2, further comprising a second electrode mechanically coupled to the device body, wherein the second electrode is configured to contact tissues of the heart when the fixation mechanism attaches to tissues of the heart.

4. The implantable medical lead of claim 3, further comprising a second leadlet mechanically supported by the device body, wherein the second leadlet mechanically supports the second electrode.

5. The implantable medical device of claim 1, wherein distal body portion is configured to cause the leadlet to extend in a direction substantially perpendicular or substantially parallel to the longitudinal axis in response to the proximal body portion rotating relative to distal body portion.

6. The implantable medical device of claim 1, wherein:
    the leadlet comprises a leadlet body extending to a leadlet distal end, and
    the leadlet body is configured to transmit a force to the leadlet distal end to cause the leadlet distal end to penetrate tissues of the heart in response to the proximal body portion rotating relative to distal body portion.

7. The implantable medical device of claim 1, wherein:
the distal body portion includes a distal marker visible on an imaging modality when implantable medical device is within a patient,
the proximal body portion includes a proximal marker visible on the imaging modality when the implantable medical device is within the patient, and
the distal marker and the proximal marker are configured to substantially align when the distal body portion has a specific rotational orientation relative to the proximal body portion.

8. The implantable medical device of claim 1, wherein the proximal body portion mechanically supports the distal body portion such that when the distal body portion exerts an action force parallel to the longitudinal axis on the proximal body portion, the proximal body portion exerts a reaction force opposite the action force on the distal body portion.

9. The implantable medical device of claim 1, wherein in response to the proximal body portion rotating relative to the distal body portion, the leadlet transitions from a stowage configuration wherein the leadlet is contained within an outer boundary defined by the device body, and a deployment configuration wherein the leadlet is extended over the extension length from the device body.

10. The implantable medical device of claim 1, wherein the device body is configured to position within a lumen of a device cup of a delivery catheter, and wherein the proximal body portion is configured to rotate around the longitudinal axis relative to the distal body portion when the device cup imparts a torque around the longitudinal axis on the proximal body portion.

11. The implantable medical device of claim 1, wherein the distal portion defines a distal end, and wherein the distal end is configured to position within the heart when the device body positions within the heart.

12. An implantable medical device configured to deliver therapy comprising:
a device body configured to position within a heart, wherein the device body comprises a proximal body portion and a distal body portion and defines a longitudinal axis extending through the proximal body portion and the distal body portion, wherein the proximal body portion is configured to rotate around the longitudinal axis relative to distal body portion, wherein the device body mechanically supports circuitry configured to deliver the therapy to the heart, and wherein the device body is configured to position the circuitry within the heart when the device body positions within the heart, and wherein the device body includes an axial portion surrounding the longitudinal axis and rotationally coupled to the proximal body portion, wherein the axial portion is configured to rotate within an inner perimeter defined by the distal body portion, the axial portion and the distal body portion defining a leadlet stowage space between the axial portion and the distal body portion;
a fixation mechanism attached to the distal body portion, wherein the fixation mechanism is configured to attach the implantable medical device to tissues of the heart; and
a leadlet mechanically coupled to the device body, wherein:
the leadlet mechanically supports an electrode configured to deliver the therapy to the heart,
the leadlet is configured to deploy from the leadlet stowage space when the proximal body portion rotates relative to distal body portion, and
the leadlet is configured to define a deployment configuration and a stowage configuration, wherein in the stowage configuration the leadlet is positioned within the leadlet stowage space and in the deployment configuration the leadlet is configured to extend from the leadlet stowage space.

13. The implantable medical device of claim 12, further comprising a second electrode mechanically coupled to the device body, wherein the second electrode is configured to contact tissues of the heart when the fixation mechanism attaches to tissues of the heart.

14. The implantable medical lead of claim 13, wherein the second electrode is rotationally coupled to the proximal body portion.

15. The implantable medical lead of claim 12, further comprising a second leadlet mechanically supported by the device body, wherein the second leadlet mechanically supports the second electrode.

16. The implantable medical device of claim 12, wherein distal body portion is configured to cause the leadlet to extend in a direction substantially perpendicular or substantially parallel to the longitudinal axis when the proximal body portion rotates relative to distal body portion.

17. The implantable medical device of claim 12, wherein:
the leadlet comprises a leadlet body extending to a leadlet distal end, and
the leadlet body is configured to transmit a force to the leadlet distal end to cause the leadlet distal end to penetrate tissues of the heart when the proximal body portion rotates relative to distal body portion.

18. The implantable medical device of claim 12, wherein:
the distal body portion includes a distal marker visible on an imaging modality when the implantable medical device is within a patient,
the proximal body portion includes a proximal marker visible on the imaging modality when the implantable medical device is within the patient, and
the distal marker and the proximal marker are configured to substantially align when the distal body portion has a specific rotational orientation relative to the proximal body portion.

19. The implantable medical device of claim 12, wherein the leadlet is mechanically coupled to the proximal body portion.

* * * * *